United States Patent [19]
Flood et al.

[11] Patent Number: 5,973,213
[45] Date of Patent: Oct. 26, 1999

[54] PROCESS FOR SEPARATING SOLIDS FROM AQUEOUS 1,4-BUTYNEDIOL SOLUTIONS

[75] Inventors: Gerald Flood, Baton Rouge, La.; Gerald Klossek; Wernfried Vondung, both of Ludwigshafen, Germany; Edmund Klausmann, Fussgönheim, Germany

[73] Assignee: BASF Aktiengesellschaft, Ludwigshafen, Germany

[21] Appl. No.: 09/000,280

[22] PCT Filed: Sep. 13, 1996

[86] PCT No.: PCT/EP96/04027

§ 371 Date: Jan. 27, 1998

§ 102(e) Date: Jan. 27, 1998

[87] PCT Pub. No.: WO97/11044

PCT Pub. Date: Mar. 27, 1997

[30] Foreign Application Priority Data

Sep. 23, 1995 [DE] Germany .......................... 195 35 450

[51] Int. Cl.⁶ ............................. C07C 27/26; C07C 31/18
[52] U.S. Cl. ............................... 568/856; 568/855
[58] Field of Search ..................... 568/855, 856, 568/861, 862, 868

[56] References Cited

U.S. PATENT DOCUMENTS

| | | | |
|---|---|---|---|
| 3,957,888 | 5/1976 | Reiss et al. | |
| 4,083,882 | 4/1978 | Taylor et al. | 568/862 |
| 4,127,734 | 11/1978 | Fremont | 568/855 |
| 4,180,687 | 12/1979 | Burrus et al. | 568/856 |
| 4,294,998 | 10/1981 | Copelin | 568/868 |
| 4,599,466 | 7/1986 | Mueller et al. | 568/861 |

FOREIGN PATENT DOCUMENTS 24 21 407   5/1974   Germany.

*Primary Examiner*—James O. Wilson
*Attorney, Agent, or Firm*—Keil & Weinkauf

[57] ABSTRACT

Solids are separated from aqueous 1,4-butynediol solutions by passing a solids-containing aqueous butynediol solution in the downflow mode through a column and thus bringing it into contact with a solvent which has a lower density than the solids-containing butynediol solution and forms a second phase with the latter, with the solvent rising in countercurrent to the aqueous butynediol solution, the solid accumulating at the interface between the aqueous butynediol and the solvent and the solid being removed from the column by taking off a mixture of aqueous butynediol and solvent.

6 Claims, No Drawings

PROCESS FOR SEPARATING SOLIDS FROM AQUEOUS 1,4-BUTYNEDIOL SOLUTIONS

The present invention relates to a process for separating solids from aqueous 1,4-butynediol solutions.

1,4-Butynediol is prepared on an industrial scale from acetylene and aqueous formaldehyde solution over copper catalysts (Weissmel, Arpe, Industrielle Organische Chemie, 2nd Edition, Verlag Chemie, p. 94). Butynediol is an important intermediate from which 1,4-butanediol can be prepared by hydrogenation, this being used as an alcohol component in polyesters and being able to be converted into tetrahydrofuran by ring closure.

Butynediol is obtained industrially as an aqueous solution containing small amounts of solids. During the preparation of butynediol, secondary reactions between $CO_2$ and formaldehyde or other intermediates in the reaction lead to the formation of red polymers which are insoluble in aqueous butynediol solution.

The polymeric solid coats all parts of the plant such as tube walls and reactor walls with a film which can be removed mechanically only with difficulty. On the other hand, if the polymeric solid remains suspended, sedimentation is uneconomical in view of the low concentration, since subsequent process steps over highly selective catalysts rule out the addition of sedimentation aids, because these have an adverse effect on the selectivity of the catalysts.

Furthermore, the butynediol solution contains solid particles which are attributable to abrasion of the catalyst. Depending on the reaction conditions in the preparation of butynediol, the proportion of abraded catalyst material is generally from 20 to 80% by weight of the solid in the aqueous solution. In general, the concentration of the solid in the aqueous butynediol solution is from about 1 to 1000 ppm. The abraded catalyst material leads to mechanical problems, particularly in pumps.

Furthermore, said solids deposit on the catalyst for the hydrogenation to butene or butanediol which generally follows the preparation of butynediol. The solid can be removed only by time-consuming and expensive stopping of plants and mechanical cleaning of affected plant parts.

It is an object of the present invention to provide a process which allows economical separation of solids from aqueous 1,4-butynediol solutions. The process should be able to be used on an industrial scale. In particular, it should be suitable for removing low concentrations of solids.

We have found that this object is achieved by a process for separating solids from aqueous 1,4-butynediol solutions, which comprises passing a solids-containing aqueous butynediol solution in the downflow mode through a column and thus bringing it into contact with a solvent which has a lower density than the solids-containing butynediol solution and forms a second phase with the latter, with the solvent rising in countercurrent to the aqueous butynediol solution, the solid accumulating at the interface between the aqueous butynediol and the solvent and the solid being removed from the column by taking off a mixture of aqueous butynediol and solvent.

The aqueous butynediol solutions to be used according to the present invention have a butynediol content which can vary within wide limits. It is generally from 25 to 75% by weight, preferably from 40 to 60% by weight and particularly preferably from 45 to 55% by weight.

The solids content of the aqueous butynediol solution used is generally from 1 to 1000 ppm, but in particular cases it can also be significantly greater, eg. up to 5% by weight. The process of the present invention is particularly advantageous for solids contents of from 2 to 500 ppm.

The removal of the solid is carried out in a column, which for the purposes of the present invention means any apparatus in which the butynediol solution can be passed from the top downward (downflow mode) in countercurrent to the solvent. On a small scale, glass columns as are used for chromatography are useful; on an industrial scale, suitable columns are, in particular, metal columns.

The butynediol solution to be purified is preferably introduced laterally into the upper part of the column. To distribute the solution uniformly in the column, customary distributor fittings such as tube distributors have been found to be useful. The butynediol solution is generally introduced into the column in such a way that the flow velocity in the column is from 0.1 to 0.4 m/min.

The butynediol solution is brought into contact with a solvent which has a lower density than the butynediol solution and forms a second phase with the latter. For this purpose, the solvents do not have to be completely immiscible with the butynediol solution to be purified. Preference is given to those solvents which dissolve in the butynediol solution to an extent of not more than 10% by weight, particularly preferably not more than 3% by weight. Specific examples are ethers such as methyl tert-butyl ether, ketones such as butyl methyl ketone, aromatic hydrocarbons such as benzene and aliphatic or cycloaliphatic hydrocarbons such as cyclohexane.

The butynediol solution is preferably brought into contact with a $C_4$–$C_{18}$-alcohol, particularly preferably a $C_8$–$C_{10}$-alcohol. Specific examples are alkanols such as hexanol, heptanol, octanol, 2-ethylhexanol and decanol, where these alkanols can be straight-chain or branched and can also be used in the form of mixtures of isomers.

The solvent is preferably introduced into the lower part of the column, with distributor fittings as in the case of the butynediol solution having been found to be useful. The flow velocity of the solvent in the column is generally selected so as to be from 0.15 to 0.4 m/min.

The volume ratio of the aqueous butynediol solution and the solvent is generally from 0.1:1 to 10:1, preferably from 0.5:1 to 3.5:1.

The column can be operated at from 0 to 100° C., preferably from 20 to 50° C. To increase the contact area between the butynediol solution and the solvent, preference is given to using packed columns. In a preferred embodiment, the column packing is arranged between the feed points for the butynediol solution and the solvent. Suitable packing elements are, for example, ceramic rings, metal rings, Pall rings and Raschig rings.

The solvent rises toward the top of the column and the solid accumulates at the interface between droplets of the aqueous butynediol solution and the solvent. At the top of the column, a solvent phase is formed. At the interface between the solvent phase at the top of the column and the butynediol solution, there is a great accumulation of solid. For this reason, a mixture of solid, butynediol and solvent is advantageously taken off at this interface and the solid is thus removed.

The solvent is advantageously discharged from the column via an overflow and returned to the process. Regulation of the amount of butynediol solution flowing out at the bottom of the column enables the height of the interface between the butynediol solution and the solvent in the column to be regulated.

In a preferred embodiment, the mixture containing the accumulated solid is taken off from the column and introduced into a separation vessel. In this vessel, the solvent and the butynediol solution separate, with the solid remaining at the interface between the two liquids or sinking into the lower butynediol phase. The solvent can be removed from the separation vessel and returned to the column. The solid accumulates to such a great extent in the butynediol solution in the separation vessel that it can be separated off by methods known per se, for example filtration, centrifugation or evaporation of the liquid, preferably by sedimentation. The butynediol solution which remains can be returned to the column or processed further.

In the process of the present invention, it is generally sufficient to remove from 0.1 to 2% by weight of the original flow of the aqueous butynediol solution to be purified from the column in the form of a mixture of solvent, butynediol and solid.

The process of the present invention removes even low concentrations of solids from aqueous butynediol solutions in an economical manner.

EXAMPLES

Examples 1–15

A column (15 cm diameter in Examples 1–11, 30 cm in Examples 12–15) containing a packing of 15 mm ceramic rings in Examples 1–11 and 2.5 cm metal rings in Examples 12–15 was supplied continuously with aqueous, 50% strength by weight butynediol solution at a point above the packing. n-Octanol in Examples 1–11 and also 14 and 15 and n-decanol in Examples 12 and 13 was introduced into the column at a point below the packing. At the interface of alcohol and the aqueous butynediol solution, 0.5% by weight of the butynediol solution fed in was taken from the column in the form of a mixture of alcohol, butynediol solution and solid. The alcohol was discharged from the column via an overflow.

The table shows further parameters of the separation experiments.

TABLE

| Example | Feed rate of butynediol solution [l/h] | Feed rate of alcohol [l/h] | Temperature [° C.] | Solids content of the butynediol solution before/after separation [ppm] | Solid separated off [%] |
|---|---|---|---|---|---|
| 1  | 150 | 180 | 36 | 56/4   | 93 |
| 2  | 160 | 180 | 35 | 74/7   | 91 |
| 3  | 150 | 180 | 45 | 37/4   | 89 |
| 4  | 160 | 180 | 42 | 70/10  | 85 |
| 5  | 150 | 180 | 36 | 50/8   | 84 |
| 6  | 140 | 140 | 26 | 95/15  | 84 |
| 7  | 160 | 190 | 36 | 104/21 | 80 |
| 8  | 120 | 180 | 80 | 78/32  | 59 |
| 9  | 250 | 100 | 40 | 90/36  | 60 |
| 10 | 70  | 200 | 40 | 90/38  | 58 |
| 11 | 50  | 250 | 40 | 90/45  | 50 |
| 12 | 250 | 500 | 22 | 192/40 | 79 |
| 13 | 250 | 600 | 26 | 25/10  | 60 |
| 14 | 200 | 700 | 27 | 160/13 | 92 |
| 15 | 450 | 550 | 32 | 200/10 | 95 |

In all experiments, at least half, in some cases even more than 90% of the solid in the feed could be separated off.

Example 16

An aqueous, 50% strength by weight butynediol solution having a content of 63 ppm was hydrogenated at 135° C. over a commercial catalyst at a weight hourly space velocity over the catalyst of 230 g of butynediol/1 of catalyst.h (Experiment A). For comparison, a butynediol solution depleted in solids according to the present invention (residue solids content: 13 ppm) was hydrogenerated (Experiment B).

|  | Experiment A | Experiment B |
|---|---|---|
| Residual butynediol content of the hydrogenation product [% by weight] | 0.25 | 0.00 |
| Residual butenediol content of the hydrogenation product [% by weight] | 1.40 | 0.14 |
| Content of by-products [% by weight] i) hydroxylbutyraldehyde | 0.28 | 0.15 |
| ii) 2-(4-hydroxybutoxy)oxolane | 0.37 | 0.02 |

Under the same conditions, the hydrogenation of the starting material treated according to the present invention was more complete than in the case of the untreated material. Removal of the solid led to reduced formation of interfering by-products.

We claim:

1. A process for separating solids from aqueous 1,4-butynediol solutions, which comprises passing a solids-containing aqueous butynediol solution in the downflow mode through a column and thus bringing it into contact with a solvent which has a lower density than the solids-containing butynediol solution and forms a second phase with the latter, with the solvent rising in countercurrent to the aqueous butynediol solution, the solid accumulating at the interface between the aqueous butynediol and the solvent and the solid being removed from the column by taking off a mixture of aqueous butynediol and solvent.

2. A process as claimed in claim 1, wherein, in a column containing column packing, the solids-containing aqueous butynediol solution is introduced above the column packing and the solvent is introduced below the column packing and the solid is removed from the column above the column packing.

3. A process as claimed in claim 1, wherein the solvent used is octanol.

4. A process as claimed in claim 1, wherein aqueous butynediol solutions having a solids content of from 1 to 1000 ppm are used.

5. A process as claimed in claim 1, wherein solids-containing aqueous butynediol solutions having a butynediol content of from 40 to 60% by weight are used.

6. A process as claimed in claim 1 wherein the mixture removed from the column, which is comprised of solids, the solvent and aqueous butynediol, is subsequently separated in a separation vessel into a solids-containing aqueous butynediol solution and the solvent, wherein the solvent is optionally returned to the column and the solids are separated by sedimentation from the aqueous butynediol solution which is optionally returned to the column.

\* \* \* \* \*